(12) United States Patent
Sato et al.

(10) Patent No.: US 9,599,475 B2
(45) Date of Patent: Mar. 21, 2017

(54) MOVEMENT STATE INFORMATION CALCULATION METHOD AND MOVEMENT STATE INFORMATION CALCULATION DEVICE

(71) Applicant: Seiko Epson Corporation, Tokyo (JP)

(72) Inventors: Akinobu Sato, Fujimi (JP); Shunichi Mizuochi, Matsumoto (JP); Shuji Uchida, Shiojiri (JP); Anand Kumar, Richmond (CA)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/766,363

(22) PCT Filed: Mar. 17, 2014

(86) PCT No.: PCT/JP2014/001521
§ 371 (c)(1),
(2) Date: Aug. 6, 2015

(87) PCT Pub. No.: WO2014/156049
PCT Pub. Date: Oct. 2, 2014

(65) Prior Publication Data
US 2016/0146610 A1    May 26, 2016

(30) Foreign Application Priority Data
Mar. 25, 2013 (JP) ................. 2013-061456

(51) Int. Cl.
*G01C 21/16* (2006.01)
*G01C 21/20* (2006.01)
(Continued)

(52) U.S. Cl.
CPC ............ *G01C 21/16* (2013.01); *A61B 5/11* (2013.01); *G01C 21/20* (2013.01); *G01C 22/006* (2013.01);
(Continued)

(58) Field of Classification Search
CPC ...... G01C 21/16; G01C 21/20; G01C 22/006; A61B 5/11; A61B 2562/0219; A61B 5/1112
(Continued)

(56) References Cited

U.S. PATENT DOCUMENTS 6,532,419 B1  3/2003  Begin et al.
7,711,483 B2  5/2010  Colley
(Continued)

FOREIGN PATENT DOCUMENTS

JP    2007-041143 A    2/2007
JP    2009-276282 A    11/2009
(Continued)

*Primary Examiner* — Brian P Sweeney
(74) *Attorney, Agent, or Firm* — Harness, Dickey & Pierce, P.L.C.

(57) ABSTRACT

A traveling direction velocity calculation device 1 calculates a posture of an acceleration sensor 10 with respect to a user, using a detection result represented in a local coordinate system associated with the acceleration sensor 10, detecting acceleration, which is worn on a user's body, when a change in the detection result of the acceleration sensor 10 satisfies a predetermined specific condition. The detection result of the acceleration sensor 10 at a time different from that when the posture is calculated and at a time when the specific condition is satisfied is transformed, using the calculated posture, to a mobile body coordinate system associated with a user. A velocity in a traveling direction of the user is calculated using the transformed detection result.

8 Claims, 14 Drawing Sheets

(51) Int. Cl.
*G01C 22/00* (2006.01)
*A61B 5/11* (2006.01)
(52) U.S. Cl.
CPC ..... *A61B 5/1112* (2013.01); *A61B 2562/0219* (2013.01)
(58) Field of Classification Search
USPC ........................................................ 701/500
See application file for complete search history.

(56) References Cited

U.S. PATENT DOCUMENTS

| | | |
|---|---|---|
| 8,718,970 B2 | 5/2014 | Uchida |
| 2010/0019963 A1 | 1/2010 | Gao et al. |
| 2013/0338915 A1 | 12/2013 | Mizuochi et al. |

FOREIGN PATENT DOCUMENTS

| | | |
|---|---|---|
| JP | 2011-149923 A | 8/2011 |
| JP | 2012-194175 A | 10/2012 |
| JP | 2013-108865 A | 6/2013 |
| JP | 2013-181900 A | 9/2013 |
| WO | WO-2007-059134 A1 | 5/2007 |

MOVEMENT STATE INFORMATION CALCULATION METHOD AND MOVEMENT STATE INFORMATION CALCULATION DEVICE

TECHNICAL FIELD

The present invention relates to a method of calculating movement state information of a user, and the like.

BACKGROUND ART

In various fields of so-called seamless positioning, motion sensing, posture control and the like, the utilization of sensors has attracted attention. As sensors, an acceleration sensor, a gyro sensor, a pressure sensor, a geomagnetic sensor and the like are widely known. A technique for calculating the positions of mobile bodies (such as, for example, a bicycle, an automobile, an electric train, a ship, and an airplane) by performing inertial navigation calculation using measurement results of sensors has also been devised.

In inertial navigation calculation, there is a problem that the accuracy of position calculation drops due to various error components which may be included in measurement results of a sensor, and thus various techniques for improving the accuracy of position calculation have been devised. For example, JP-A-2012-194175 discloses a technique in which, with a mobile body such as four-wheeled automobile as a target, the installation posture of a sensor with respect to the mobile body is determined, and the position or velocity of the mobile body is calculated.

SUMMARY OF INVENTION

Technical Problem

There is a problem in a case where the technique of JP-A-2012-194175 is applied to a person. In the technique of JP-A-2012-194175, it is assumed that the mobile body is fixed in shape, and that the posture of the sensor is also fixed. That is, it is assumed that the posture of the sensor is fixed in the moving direction of the mobile body. However, a person is not fixed in shape. During movement, not only the arms and legs but also the body is associated with operations such as a twist or a vertical motion. For this reason, even when the posture of the sensor with respect to an installed region is fixed, the region itself moves. Specifically, the relative posture of the sensor (to put it generally, "the posture of the sensor with respect to a user" may also be said) based on the moving direction of a user can be changed. Therefore, when the technique of JP-A-2012-194175 is applied to a person as it is, there is a problem in that the position or velocity of a user is not appropriately calculated.

Solution to Problem

An advantage of some aspects of the invention is to propose a new method for appropriately calculating any of the position and velocity of a user (hereinafter, referred to as "movement state information" collectively).

According to a first aspect of the invention, there is provided a movement state information calculation method including: calculating a posture of a sensor with respect to a user, using a detection result represented in a coordinate system associated with the sensor, detecting any of a velocity and acceleration, which is worn on a user's body, when a change in the detection result satisfies a predetermined specific condition; transforming the detection result at a time different from that when the posture is calculated and at a time when the specific condition is satisfied, using the posture, to a mobile body coordinate system associated with the user; and calculating any of a position and a velocity (movement state information) of the user, using the transformed detection result.

In addition, according to another aspect of invention, there may be provided a movement state information calculation device including: a sensor, detecting any of a velocity and acceleration, which is worn on a user's body; a posture calculation unit that calculates a posture of the sensor with respect to the user, using a detection result of the sensor represented in a coordinate system associated with the sensor when a change in the detection result satisfies a predetermined specific condition; a coordinate transformation matrix calculation unit that calculates a coordinate transformation matrix which is used for transforming the detection result at a time different from that when the posture is calculated and at a time when the specific condition is satisfied, using the posture, to a mobile body coordinate system associated with the user; and a movement state information calculation unit that calculates movement state information of the user, using the coordinate transformation matrix, and the detection result at a time different from that when the posture is calculated and at a time when the specific condition is satisfied.

According to the first aspect and the like of the invention, the posture of the sensor with respect to the user is calculated using the detection result of the sensor, detecting any of a velocity and acceleration, which is worn on the user's body, when a change in the detection result of the sensor satisfies the predetermined specific condition. The detection result at a time different from that when the posture is calculated and at a time when the specific condition is satisfied is transformed, using the calculated posture, from a sensor coordinate system to a mobile body coordinate system associated with the user, and movement state information of the user is calculated using the transformed detection result. The posture is calculated using the detection result of the sensor when a change in the detection result of the sensor satisfies the predetermined specific condition, and thus it is possible to calculate the posture of the sensor in a certain specific operation state of the user. This posture is used for coordinate transformation of the detection result of the sensor in the same operation state as that when the posture is calculated, and thus it is possible to appropriately perform coordinate transformation from the sensor coordinate system to the mobile body coordinate system. Therefore, it is possible to appropriately calculate movement state information of the user.

In addition, the movement state information calculation method of a second aspect of the invention may further include correcting a value of a component other than a traveling direction component of the user included in the transformed detection result.

According to the second aspect of the invention, a value of a component other than a traveling direction component of the user included in the transformed detection result is corrected. The detection result in the same operation state as that when the posture is calculated is corrected, and thus it is possible to appropriately correct a value of a component other than in a traveling direction component of the user.

In addition, in the movement state information calculation method of a third aspect of the invention, calculating the movement state information may include: calculating an amplitude of acceleration in a traveling direction of the user, using the transformed detection result; and calculating a velocity in a traveling direction of the user on the basis of the amplitude.

Although the details will be described in the embodiments, it is obvious that there is a correlation between the amplitude of acceleration in the traveling direction of the user and the velocity in the traveling direction of the user. Therefore, as in the third aspect of the invention, it is possible to calculate the amplitude of acceleration in the traveling direction of the user using the transformed detection result of the sensor, and to appropriately calculate the velocity in the traveling direction of the user based on the amplitude.

In addition, in the movement state information calculation method of a fourth aspect of the invention, calculating the posture may include determining a timing at which the specific condition is satisfied on the basis of a change in a vertical velocity which is obtained from the detection result of the coordinate system associated with the sensor.

According to the fourth aspect of the invention, based on a change in the vertical velocity which is obtained from the detection result of the sensor of the coordinate system associated with the sensor, it is possible to appropriately determine a timing at which the specific condition is satisfied.

In addition, in the movement state information calculation method of a fifth aspect of the invention, determining the timing may include determining that the specific condition is satisfied when the vertical velocity is set to a value of a central portion in a varying range, and a direction of change of the velocity is an increasing direction or a decreasing direction.

According to the fifth aspect of the invention, when the vertical velocity is set to a value of a central portion in a varying range, and the direction of change of the velocity is an increasing direction or a decreasing direction, it is determined that the specific condition is satisfied. A case where the condition is satisfied refers to, for example, a case where the user lands on a ground surface during walking or during running, or the foot is away from the ground surface and the body reaches a highest point, and these timings can be determined as a timing at which the specific condition is satisfied.

In addition, in the movement state information calculation method of a sixth aspect of the invention, the sensor may be worn on a predetermined region other than an arm of the user.

According to the sixth aspect of the invention, the sensor is worn on a predetermined region other than the user's arm. For this reason, the posture of the sensor worn on the predetermined region other than the arm with respect to the user is appropriately determined in combination with the movement state calculation method, and thus it is possible to appropriately calculate movement state information of the user.

DESCRIPTION OF EMBODIMENTS

Hereinafter, examples of preferred embodiments of the invention will be described with reference to the accompanying drawings. Embodiments to which the invention can be applied are, of course, not limited to embodiments described below.

1. First Embodiment 1-1. System Configuration

Figure 1:
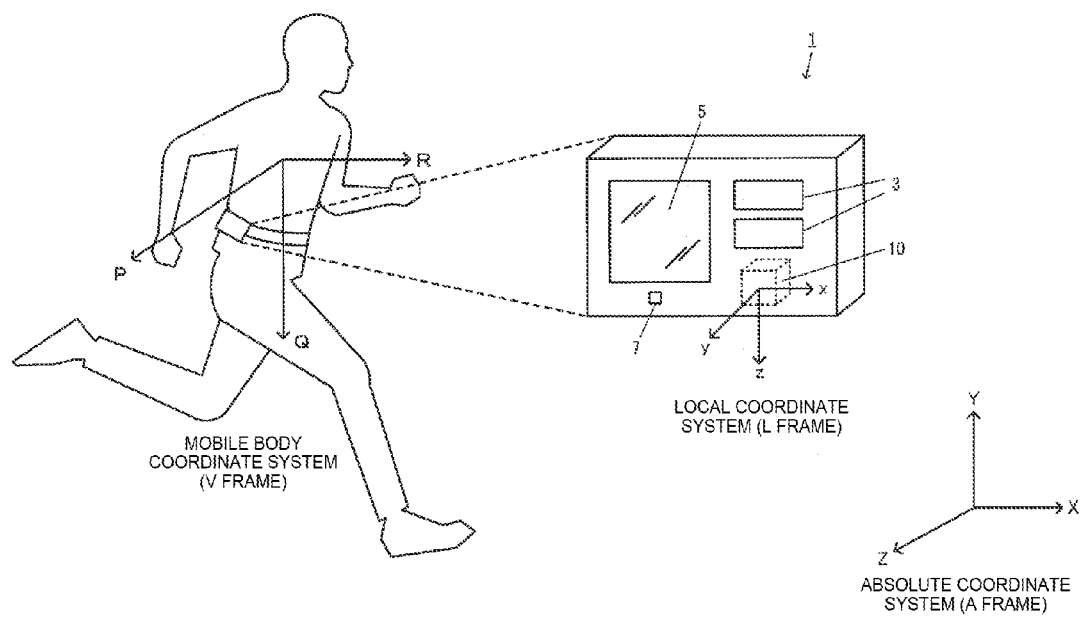
FIG. 1 is a diagram illustrating a configuration example of the entire system of a traveling direction velocity calculation device.

FIG. 1 is a diagram illustrating a configuration example of the entire system of a traveling direction velocity calculation device 1 in the present embodiment. The traveling direction velocity calculation device 1 is, for example, a small-sized electronic device which is used in a state where the device is worn on a user's waist (right of waist or left of waist), and is a type of movement state information calculation device that calculates a velocity in a direction in which a user travels (hereinafter, appropriately referred to as "traveling direction velocity") as movement state information.

The traveling direction velocity calculation device 1 is configured to include, as main components, operation buttons 3 which are an input device for a user to input various operations relating to the calculation of a traveling direction velocity, a liquid crystal display 5 on which information such as the calculated traveling direction velocity is displayed, a speaker 7, an acceleration sensor 10, and a control board which is not shown.

In the present embodiment, three types of coordinate system are defined. A first coordinate system is a local coordinate system which is a three-dimensional orthogonal coordinate system (sensor coordinate system) associated with the acceleration sensor 10 which is included in the traveling direction velocity calculation device 1. In the present specification, the local coordinate system is also referred to as an L (Local) frame. In the present embodiment, three axes of the local coordinate system are denoted by an x-axis, a y-axis and a z-axis.

A second coordinate system is a three-dimensional orthogonal coordinate system (mobile body coordinate system) associated with a mobile body. In the present specification, the mobile body coordinate system is also referred to as a V (Vehicle) frame. In the present embodiment, a front-back direction in which the front of a user is set to be positive is set to a roll axis (R-axis), a horizontal direction in which the right side is set to be positive is defined as a pitch axis (P-axis), and an up-and-down direction in which a vertical downward direction is set to be positive is defined as a yaw axis (Q-axis).

A third coordinate system is a three-dimensional orthogonal coordinate system (absolute coordinate system) which is a coordinate system determining the moving space of a mobile body. In the present specification, the absolute coordinate system is also referred to as an A (Absolute) frame. The A frame is defined as, for example, an NED coordinate system known as a north east down coordinate system, or an ECEF coordinate system known as an earth centered earth fixed coordinate system. In the present embodiment, three axes of the absolute coordinate system are denoted by an X-axis, a Y-axis and a Z-axis.

The acceleration sensor 10 is a sensor which is mounted on the traveling direction velocity calculation device 1, and detects an acceleration vector of a user. As the acceleration sensor 10, for example, a MEMS (Micro Electro Mechanical Systems) sensor is used. A value measured by the acceleration sensor 10 is set to acceleration of a mobile body measured in the local coordinate system.

The traveling direction velocity calculation device 1 is worn on a user's waist in a posture as shown in FIG. 1. Therefore, the z-axis of the acceleration sensor 10 is set to a vertical axis.

The acceleration or velocity of a user has a direction and a magnitude. For this reason, in the present specification, a scalar and a vector will be described appropriately distinctively. In principle, when acceleration or velocity is referred to, the magnitude (scalar quantity) of acceleration or velocity is assumed to be expressed, and when an acceleration vector or a velocity vector is referred to, acceleration and velocity considering a direction and magnitude are assumed to be expressed.

Meanwhile, in order to clarify quantities defined in each coordinate system, the type of coordinate system is expressed at the beginning of wording indicating each of the quantities, and the description thereof will be given. For example, an acceleration vector represented in the local coordinate system is called a "local coordinate acceleration vector", and an acceleration vector represented in the absolute coordinate system is called an "absolute coordinate acceleration vector". The same is true of other quantities.

In addition, the posture of a sensor is represented by an Euler angle such as a roll angle, a pitch angle and a yaw angle. The direction of a sensor represented in the absolute coordinate system is represented as an "absolute posture", and the posture angle thereof is called an "absolute posture angle". In addition, the relative posture (relative posture) of a sensor with respect to a user is represented as a "sensor posture", and the posture angle (relative posture angle) thereof is called a "sensor posture angle".

In addition, in the drawings referred to in the following description, blocks of various types of sensors are shown by a double line, and processing blocks in which a calculation process is performed using measurement results of a sensor are shown by a single line.

The control board includes a processing unit 100 having a CPU (Central Processing Unit), a DSP (Digital Signal Processor), an ASIC (Application Specific Integrated Circuit) and the like, a communication unit 500 having an interface IC or a connection terminal for realizing data transmission and reception to and from an external device, and a storage unit 600 having various IC memories such as a ROM (Read Only Memory), a flash ROM, or a RAM (Random Access Memory), a recording medium such as a hard disk, and the like.

1-2. Functional Configuration

Figure 2:
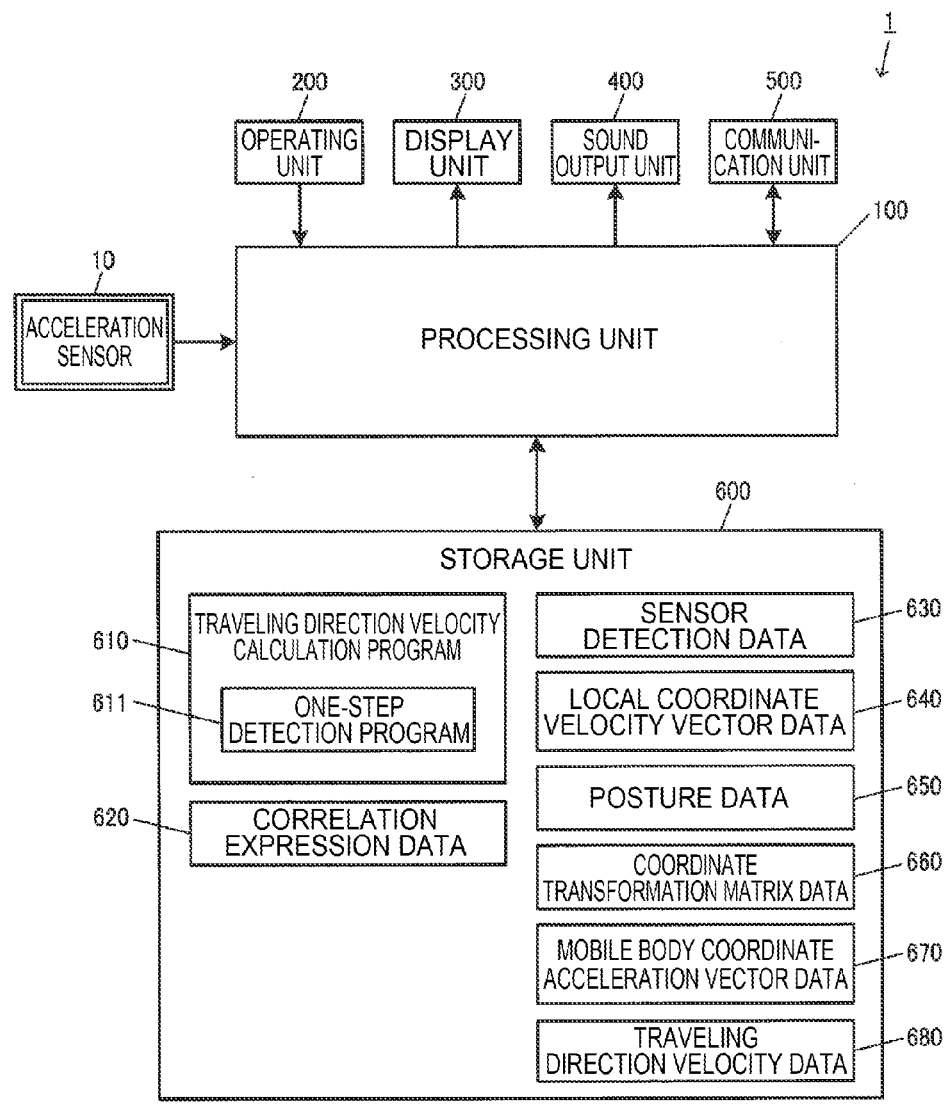
FIG. 2 is a diagram illustrating an example of a functional configuration of a traveling direction velocity calculation device.

FIG. 2 is a diagram illustrating an example of a functional configuration of the traveling direction velocity calculation device 1.

The traveling direction velocity calculation device 1 is configured to include the acceleration sensor 10, the processing unit 100, an operating unit 200, a display unit 300, a sound output unit 400, the communication unit 500, and the storage unit 600.

The processing unit 100 controls each unit of the traveling direction velocity calculation device 1, as a whole, in accordance with various programs such as a system program which is stored in the storage unit 600.

Figure 3:
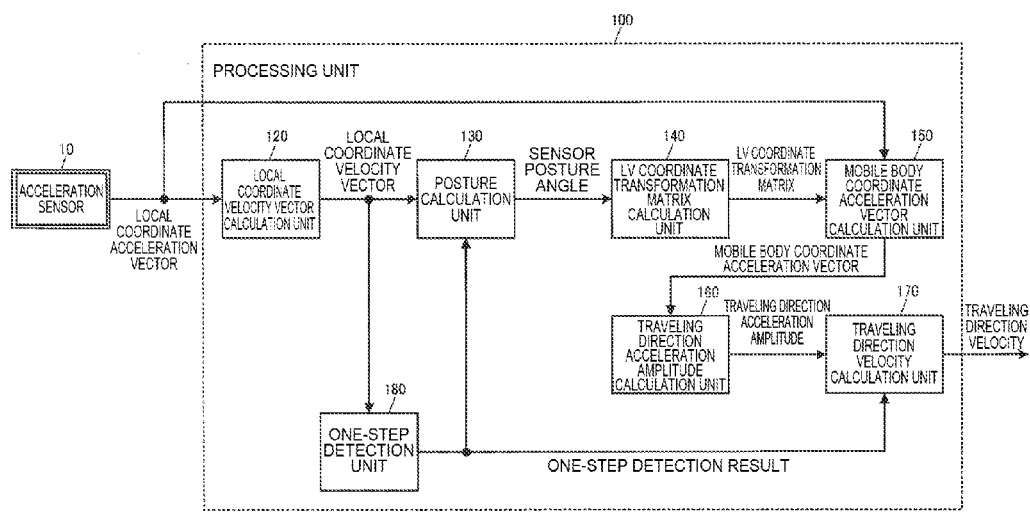
FIG. 3 is a diagram illustrating a functional block of a processing unit.

FIG. 3 is a functional block diagram illustrating an outline of a functional configuration of the processing unit 100.

The processing unit 100 includes, as functional units, a local coordinate velocity vector calculation unit 120, a posture calculation unit 130, an LV coordinate transformation matrix calculation unit 140, a mobile body coordinate acceleration vector calculation unit 150, a traveling direction acceleration amplitude calculation unit 160, a traveling direction velocity calculation unit 170, and a one-step detection unit 180.

The local coordinate velocity vector calculation unit 120 integrates and adds local coordinate acceleration vectors which are input from the acceleration sensor 10, and calculates a local coordinate velocity vector. In the present embodiment, "integration" means that values over a predetermined time are cumulatively summed. In addition, "addition" means that a result obtained by the integration is added to a result which is finally updated.

Specifically, the local coordinate velocity vector calculation unit 120 integrates local coordinate acceleration vectors over a predetermined time, to thereby calculate the amount of change of a velocity vector represented in the local coordinate system during the predetermined time. The calculated amount of change of the velocity vector is added to a local coordinate velocity vector which is finally updated, and thus the local coordinate velocity vector is newly calculated and updated.

The posture calculation unit 130 determines a sensor posture using the local coordinate velocity vector calculated by the local coordinate velocity vector calculation unit 120. The posture calculation unit 130 determines the posture of a sensor with respect to a user at a timing when one step of a user is detected by the one-step detection unit 180.

The term "posture of a sensor" as used herein means, for example, the relative posture of a sensor in a reference direction relating to traveling such as the traveling direction of a user. Even when the posture of a sensor for an attachment region does not change, the attachment region itself moves along with the movement. That is, the region to which a sensor is attached is relatively displaced in a reference direction relating to traveling. For this reason, the posture of a sensor also relatively changes in the reference direction relating to traveling. This changeable posture of a sensor is determined.

Meanwhile, the posture of a sensor in the reference direction relating to traveling can refer to the posture of a sensor with respect to a user on the whole, and thus the wording is represented as the latter in the present specification. In addition, the calculation of a posture refers to the calculation of a posture angle.

There is a relationship of the following Expression (1) between the velocity vector (local coordinate velocity vector) represented in the local coordinate system and the velocity vector (mobile body coordinate velocity vector) represented in the mobile body coordinate system.

Expression 1

$$\begin{bmatrix} v_R^V \\ v_P^V \\ v_Q^V \end{bmatrix} = C_L^V \begin{bmatrix} v_x^L \\ v_y^L \\ v_z^L \end{bmatrix} \quad (1)$$

In expressions used in the present specification, a component of the velocity vector is indicated by the lower-case letter "v". In addition, in the notation of the velocity vector, the type of a coordinate system is indicated by the suffix of a superscript capital letter. "L" means the local coordinate system, "V" means the mobile body coordinate system, and "A" means the absolute coordinate system. In addition, a component of each axis in a corresponding coordinate system is indicated by the suffix of a subscript lower-case letter. For example, in a case of three axes of the local coordinate system, the notation of "x", "y" and "z" is used.

In addition, in the present specification, a coordinate transformation matrix is indicated by the capital letter "C". In each coordinate transformation matrix, a subscript suffix indicates a coordinate system before coordinate transformation, and a superscript suffix indicates a coordinate system after coordinate transformation. For example, "$C_L^V$" indicates a coordinate transformation matrix from the local coordinate system (L frame) to the mobile body coordinate system (V frame), and "$C_A^L$" indicates a coordinate transformation matrix from the absolute coordinate system (A frame) to the local coordinate system (L frame).

Here, a restriction condition relating to the moving direction of a user is applied. Specifically, velocity components in the longitudinal and transverse directions (vertical direction and horizontal direction) of a user are assumed to be zero, and a restriction condition is set in which velocity components in the Q-axis direction and the P-axis direction of the mobile body coordinate system (V frame) are assumed to be zero. That is, a restriction condition is set in which a relation of $\{v_P^V = v_Q^V = 0\}$ is established with respect to the velocity of a user.

In this case, from Expression (1), a pitch angle "θ" which is a pitch component of the sensor posture and a yaw angle "ψ" which is a yaw component can be calculated as in the following Expressions (2) and (3).

Expression 2

$$\theta = \arctan \frac{-v_z^L}{\sqrt{(v_x^L)^2 + (v_y^L)^2}} \quad (2)$$

Expression 3

$$\psi = \arctan 2(v_y^L, v_x^L) \quad (3)$$

The pitch angle "θ" and the yaw angle "ψ" indicate rotation angles of a sensor around the P-axis and the Q-axis of the mobile body coordinate system, respectively. That is, it may be said that the pitch angle "θ" and the yaw angle "ψ" indicate relative posture angles of a sensor with respect to a user.

The LV coordinate transformation matrix calculation unit 140 calculates a coordinate transformation matrix (hereinafter, called an "LV coordinate transformation matrix") from the local coordinate system to the mobile body coordinate system, using the sensor posture angle determined by the posture calculation unit 130. Meanwhile, the LV coordinate transformation matrix itself is publicly known, and thus a description using expressions or the like will not be given.

The mobile body coordinate acceleration vector calculation unit 150 performs coordinate transformation on the local coordinate acceleration vector which is input from the acceleration sensor 10, using the LV coordinate transformation matrix calculated by the LV coordinate transformation matrix calculation unit 140, to thereby calculate a mobile body coordinate acceleration vector.

The traveling direction acceleration amplitude calculation unit 160 calculates the amplitude of acceleration in the traveling direction of a user (hereinafter, referred to as a "traveling direction acceleration amplitude") on the basis of the mobile body coordinate acceleration vector calculated by the mobile body coordinate acceleration vector calculation unit 150. The details thereof will be described later.

The traveling direction velocity calculation unit 170 calculates the traveling direction velocity of a user, using the traveling direction acceleration amplitude calculated by the traveling direction acceleration amplitude calculation unit 160. The traveling direction velocity calculation unit 170 is equivalent to a movement state information calculation unit that calculates movement state information of a user, using the posture of a sensor with respect to the user and the detection result of the sensor.

The one-step detection unit 180 detects one step of the user on the basis of the local coordinate velocity vector calculated by the local coordinate velocity vector calculation unit 120. The details thereof will be described later.

Here, a description will be given of a calculation timing of the sensor posture based on the posture calculation unit 130 and a calculation timing of the traveling direction velocity based on the traveling direction velocity calculation unit 170.

Figure 4:
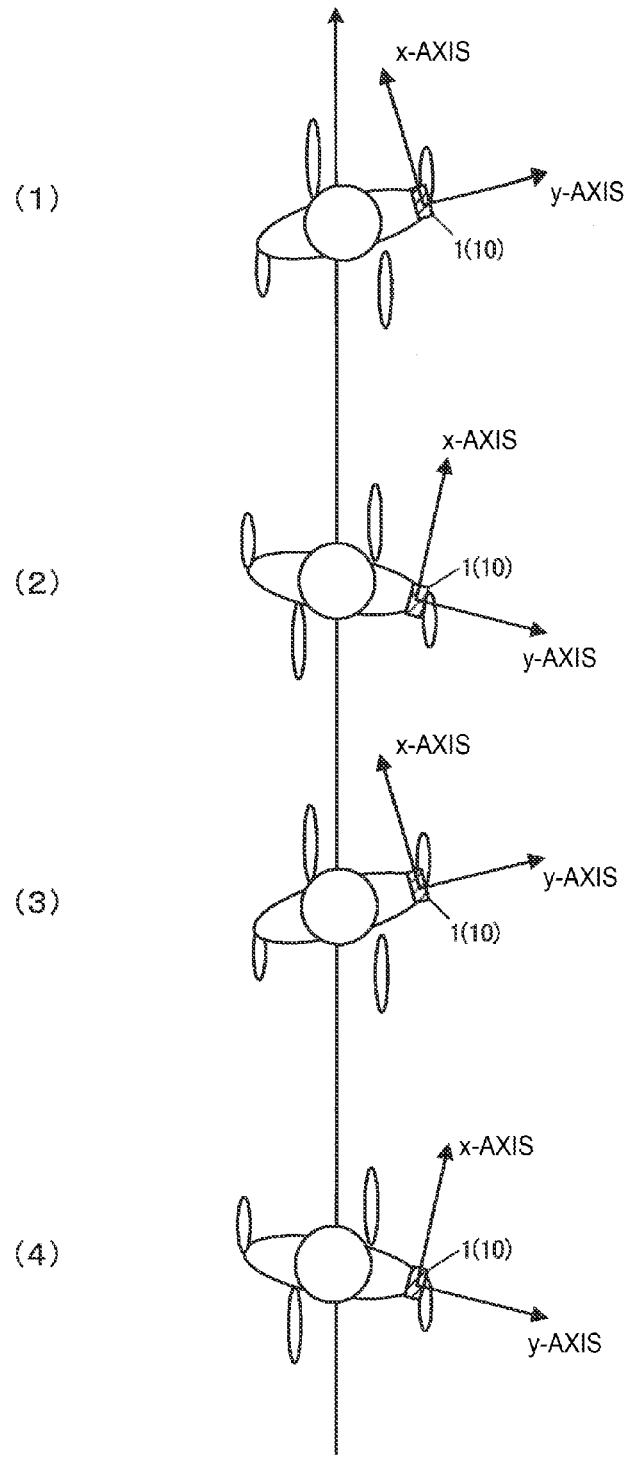
FIG. 4 is a diagram illustrating a principle.

FIG. 4 is an overhead view illustrating the movement of a user when the user who wears the traveling direction velocity calculation device 1 on the right of his/her waist performs a walking motion. A case where the traveling direction velocity calculation device 1 is worn on the right of the user's waist will be illustrated and described.

The axis in a front-back direction based on a user is an axis (R-axis) in a traveling direction. The sensor posture of the acceleration sensor 10 with respect to the user changes at any time in association with a walking motion or a running motion of the user. In a state where the user takes a step with his/her right foot, as shown in (2) or (4) of the drawing, the coordinate system (local coordinate system) of the acceleration sensor 10 is set to be in a state of being rotated clockwise in the traveling direction. On the other hand, in a state where the user takes a step with his/her left foot, as shown in (1) or (3) of the drawing, the coordinate system (local coordinate system) of the acceleration sensor 10 is set to be in a state of being rotated counterclockwise in the traveling direction.

That is, a relationship between the local coordinate system and the mobile body coordinate system changes periodically in association with the walking motion of the user. Consequently, in the present embodiment, the sensor posture of the acceleration sensor 10 is determined at any one timing. Thereafter, at a timing when it is considered that the sensor posture at the above timing during the walking motion and the posture of the user become the same as each other, the traveling direction velocity of the user is calculated using the sensor posture which is determined in advance.

Figure 5:
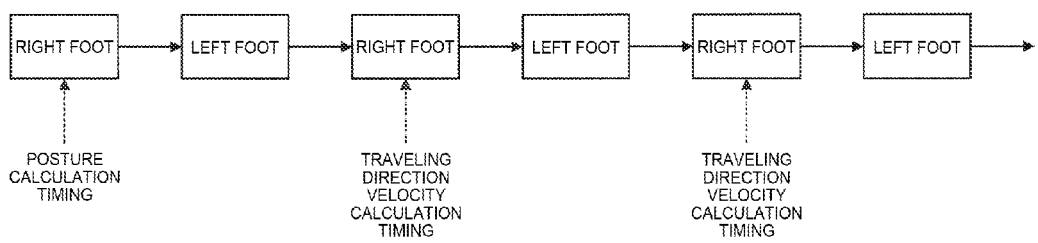
FIG. 5 is a diagram illustrating a principle.

FIG. 5 is a diagram illustrating calculation timings of the sensor posture and calculation timings of the traveling direction velocity.

Initially, the sensor posture of the acceleration sensor 10 is determined at a timing of the user's right foot (timing between landing of the left foot and landing of the right foot). Next, no action is performed at a timing of the left foot (the same timing between landing of the right foot and landing of the left foot), and at the next timing of the right foot, the velocity in the traveling direction is calculated using the sensor posture which is determined in advance. After this, the velocity in the traveling direction is calculated at the timing of the right foot.

Figure 6:
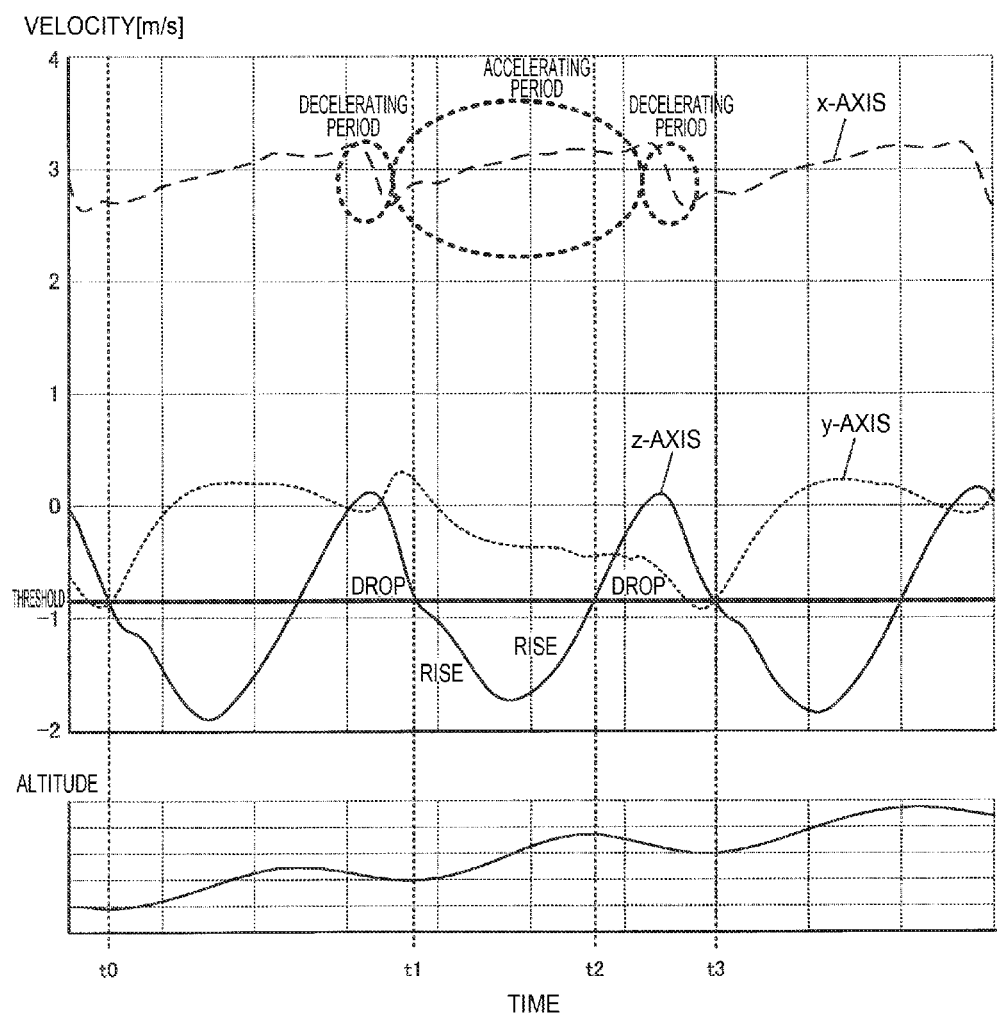
FIG. 6 is a diagram illustrating a principle.

FIG. 6 is a diagram illustrating a variation over time of each component of the local coordinate velocity vector obtained by performing an experiment in which a test subject who wears the traveling direction velocity calculation device 1 of the present embodiment as shown in FIG. 1 runs at a constant velocity. The variation over time of a velocity component in the x-axis direction is shown by a broken line, the variation over time of a velocity component in the y-axis direction is shown by a dotted line, and the variation over time of the velocity component in the z-axis direction is shown by a solid line. In addition, the lower portion of the drawing shows a height component (altitude) of the position of the traveling direction velocity calculation device 1.

In FIG. 6, in a periodic timing, it may be said that the posture of the sensor with respect to the user is constant. A detailed description is as follows.

First, times t1 to t3 show a change in one step of the user. The user's left foot lands around time t1 by decreasing the velocity in the x-axis direction, the altitude of the body reaches a highest point around time t2 due to inversion of the vertical velocity (velocity in the z-axis direction) of the body, and then the reverse right foot lands around time t3 by decreasing the velocity in the x-axis direction due to inversion of the vertical velocity of the body. At any of a timing at which landing occurs (hereinafter, referred to as a "landing timing") and a timing at which the body reaches the highest point (hereinafter, referred to as a "highest point arrival timing"), it can be understood that the vertical velocity (velocity in the z-axis direction) of the user traverses an approximately central value (heavy line of FIG. 6) of a change in the vertical velocity.

Here, when focusing on time t0 and time t3, both times t0 and t3 are landing timings of the right foot, and it may be said that the velocities of the x-axis, the y-axis, and the z-axis are substantially constant. However, at time t1 which is the landing timing of the left foot and time t3 which is the landing timing of the right foot, for example, the velocity of the y-axis varies greatly. It may be said that this shows that the posture of the sensor with respect to the user is constant between the landing timings from the right foot to the right foot and between the landing timings from the left foot to the left foot. Meanwhile, the same is true of the highest point arrival timing. It may be said that the posture of the sensor is fixed at the highest point arrival timings (or the reverse timings) between landing of the right foot and landing of the left foot.

Consequently, in the present embodiment, the highest point arrival timing between landing of one foot determined in advance and landing of the other foot is set to a reference timing, and the sensor posture at this reference timing is estimated to be fixed. The traveling direction velocity is assumed to be calculated whenever this reference timing arrives.

The highest point arrival timing is a timing equivalent to a timing at which a change in the detection result of the sensor satisfies a predetermined specific condition. The determination of this highest point arrival timing is set to a value of the central portion of a range in which the vertical velocity changes, and is a timing at which the direction of change of the velocity is set to an increasing direction. In the present embodiment, at an even-numbered or odd-numbered timing (that is, every other highest point arrival timing) of a count value which is counted whenever the highest point arrival timing arrives, the traveling direction velocity is calculated. In this manner, it is possible to detect the highest point arrival timing between landing of the right foot and landing of the other foot (left foot).

Meanwhile, the value of a central portion does not necessarily mean a central value between a maximum value and a minimum value strictly, and means an approximately central value (for example, value within a range of ±10% of the central value).

Referring back to FIG. 2, the operating unit 200 is configured to include, for example, an input device such as a touch panel or a button switch, and outputs an operation signal according to an executed operation to the processing unit 100. Various instructions such as a calculation instruction for the traveling direction velocity are input by the operation of the operating unit 200. The operating unit 200 is equivalent to the operation buttons 3 of FIG. 1.

The display unit 300 is configured to include, for example, a display device such as an LCD (Liquid Crystal Display), and performs various displays based on a display signal which is input from the processing unit 100. Information such as the calculated traveling direction velocity is displayed on the display unit 300. The display unit 300 is equivalent to the liquid crystal display 5 of FIG. 1.

The sound output unit 400 is configured to include, for example, a sound output device such as a speaker, and performs various sound outputs based on an audio signal which is input from the processing unit 100. The sound output unit 400 is equivalent to the speaker 7 of FIG. 1.

The communication unit 500 is a communication device for transmitting and receiving information used inside the device, calculated results or the like to and from an external information control device. As a communication system of the communication unit 500, various systems such as a wired connection system using a cable based on a predetermined communication standard or a wireless connection system using near-field communication can be applied. In the communication system, either a wired system or a wireless system may be used.

The storage unit 600 is realized by a storage device such as, for example, a ROM, a flash ROM, or a RAM, and stores a system program for the processing unit 100 to control the traveling direction velocity calculation device 1 as a whole, various programs for executing various application processes, data, or the like.

A traveling direction velocity calculation program 610 which is read out by the processing unit 100 and is executed as a traveling direction velocity calculation process (see FIG. 8) is stored in the storage unit 600. The traveling direction velocity calculation program 610 includes a one-step detection program 611 which is executed as a one-step detection process (see FIG. 9), as a subroutine.

In addition, the storage unit 600 stores correlation expression data 620, sensor detection data 630, local coordinate velocity vector data 640, posture data 650, coordinate transformation matrix data 660, mobile body coordinate acceleration vector data 670, and traveling direction velocity data 680.

Figure 7:
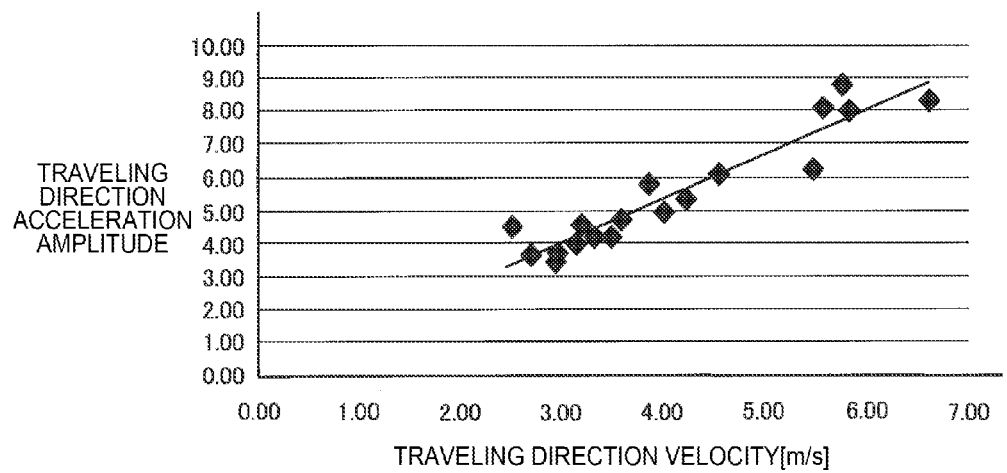
FIG. 7 is a diagram illustrating correlation expression data.

FIG. 7 is a diagram illustrating the correlation expression data 620. The correlation expression data 620 is data in which a relationship between the traveling direction velocity and the traveling direction acceleration amplitude is determined. The correlation expression data may be data of a function expression, and may be data of a table form which is capable of being searched for one side from the other.

According to research of the inventor, it can be understood that the traveling direction velocity and the traveling direction acceleration amplitude have a positive correlation therebetween. FIG. 7 is a diagram illustrating the positive correlation. In FIG. 7, each plot having a diamond shape shows the traveling direction acceleration amplitude at the experimental traveling direction velocity. According to this, there is a positive correlation between the traveling direction velocity and the traveling direction acceleration amplitude. Consequently, data showing this correlation characteristics is the correlation expression data 620. Hitherto, it has been known that there is a positive correlation between the vertical acceleration amplitude and the traveling direction velocity. However, according to research of the inventor, it can be understood that the vertical acceleration amplitude and the traveling direction velocity have a correlation when a user walks, but no positive correlation is shown when a user runs (not shown).

Meanwhile, the traveling direction acceleration amplitude in the present embodiment means a difference between a maximum value and a minimum value in a variation over time of traveling direction acceleration. However, when half the value of the difference between a maximum value and a minimum value in a variation over time of traveling direction acceleration is set to the traveling direction acceleration amplitude, approximately the same result is obtained, and any definition may be, of course, adopted.

Referring back to FIG. 2, the sensor detection data 630 is data in which the local coordinate acceleration vector detected by the acceleration sensor 10 is stored in a time-series manner.

The local coordinate velocity vector data 640 is data in which the local coordinate velocity vector calculated by the local coordinate velocity vector calculation unit 120 is stored in a time-series manner.

The posture data 650 is data in which the sensor posture angle calculated by the posture calculation unit 130 is stored.

The coordinate transformation matrix data 660 is data in which the LV coordinate transformation matrix calculated by the LV coordinate transformation matrix calculation unit 140 is stored.

The mobile body coordinate acceleration vector data 670 is data in which the mobile body coordinate acceleration vector calculated by the mobile body coordinate acceleration vector calculation unit 150 is stored in a time-series manner.

The traveling direction velocity data 680 is data in which the traveling direction velocity calculated by the traveling direction velocity calculation unit 170 is stored in a time-series manner.

1-3. Flow of Processes

Figure 8:
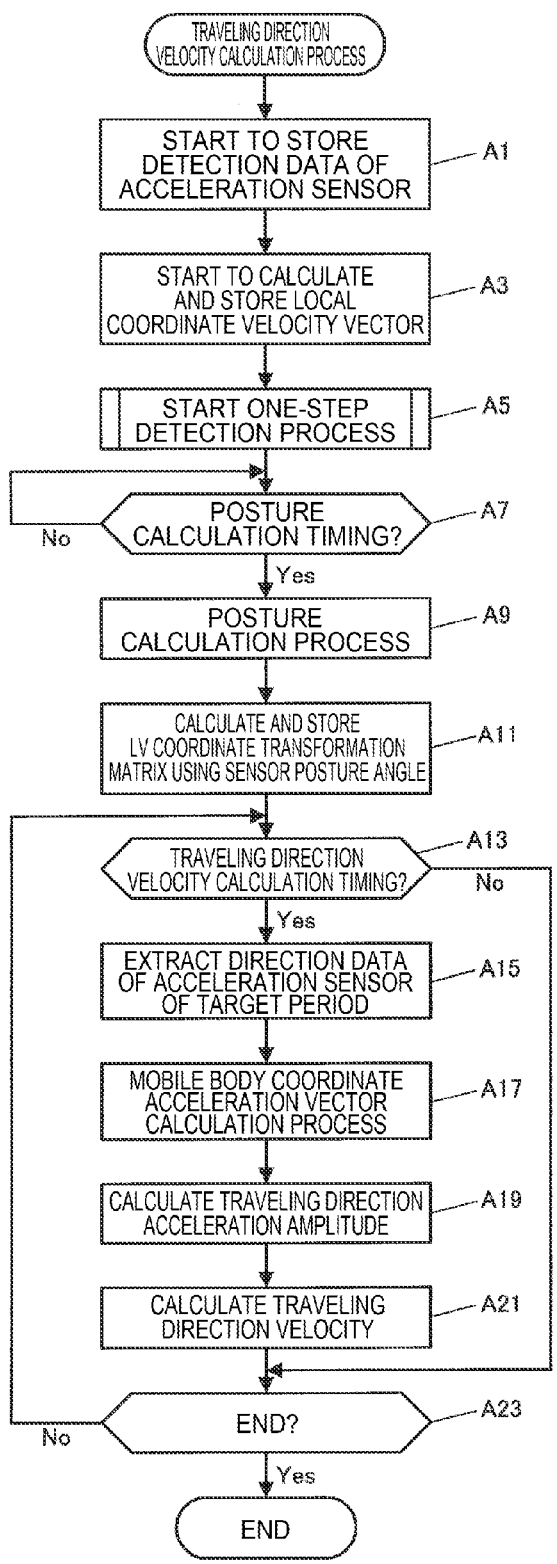
FIG. 8 is a flow diagram illustrating a flow of a traveling direction velocity calculation process.

FIG. 8 is a flow diagram illustrating a flow of a traveling direction velocity calculation process which is executed by the processing unit 100 in accordance with the traveling direction velocity calculation program 610 which is stored in the storage unit 600.

Initially, the processing unit 100 starts a process of storing the detection result of the acceleration sensor 10 in the sensor detection data 630 of the storage unit 600 (step A1). Next, the local coordinate velocity vector calculation unit 120 starts the calculation of the local coordinate velocity vector and a process of storing the calculated local coordinate velocity vector in the local coordinate velocity vector data 640 of the storage unit 600, using the detection result of the acceleration sensor 10 (step A3).

Thereafter, the one-step detection unit 180 starts a one-step detection process in accordance with the one-step detection program 611 which is stored in the storage unit 600 (step A5).

Figure 9:
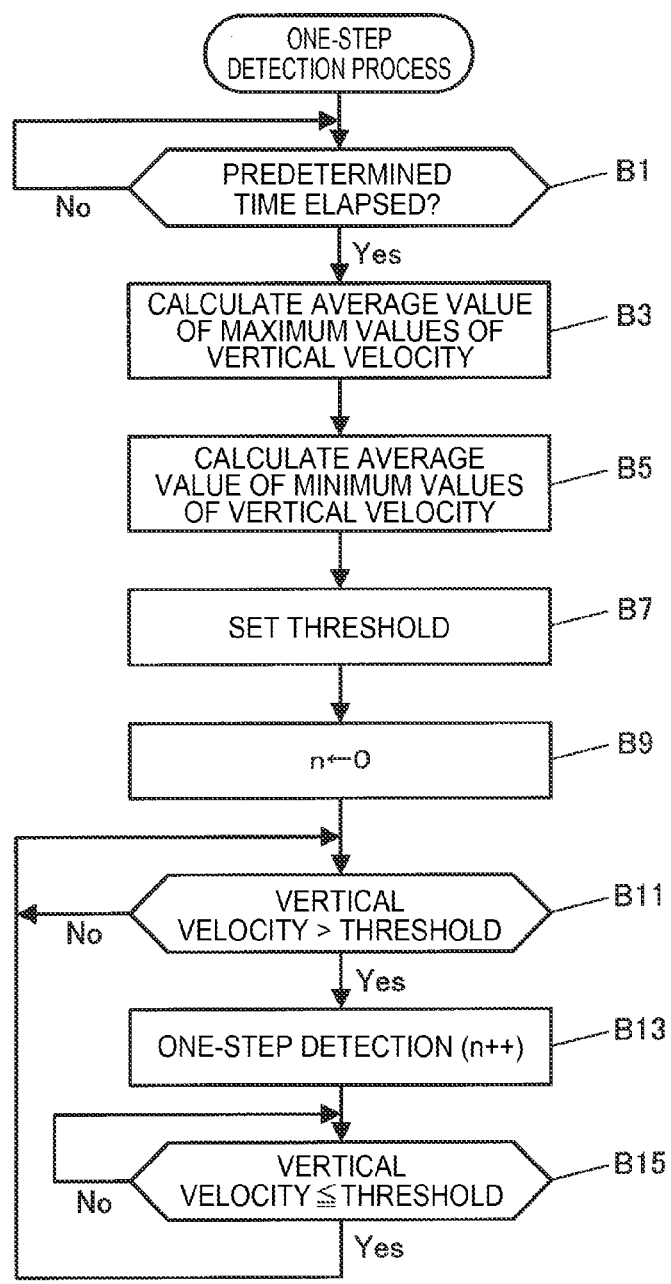
FIG. 9 is a flow diagram illustrating a flow of a one-step detection process.

FIG. 9 is a flow diagram illustrating a flow of the one-step detection process.

The one-step detection unit 180 stores data until a predetermined time has elapsed in order to acquire sample data (step B1; No). That is, during the predetermined time, the local coordinate velocity vector is calculated on the basis of detection data of the acceleration sensor 10, to store data. When the predetermined time has elapsed (step B1; Yes), the one-step detection unit 180 performs a process (step B3) of calculating an average value of maximum values of the vertical velocity and a process (step B5) of calculating an average value of minimum values of the vertical velocity, on the basis of the accumulated data.

Next, the one-step detection unit 180 sets a threshold (step B7). The threshold can be set to, for example, a value obtained by averaging the average value of maximum values of the vertical velocity calculated in step B3 and the average value of the minimum values of the vertical velocity calculated in step B5.

Thereafter, the one-step detection unit 180 resets a counter "n" used for counting the number of steps taken, to zero (step B9). Next, the one-step detection unit 180 determines whether the vertical velocity has exceeded the threshold (step B11), and stands by as it is when the unit determines that the vertical velocity has not exceeded the threshold (step B11; No). On the other hand, when it is determined that the vertical velocity has exceeded the threshold (step B11; Yes), the one-step detection unit 180 increases the counter "n" by 1 (step B13).

Thereafter, the one-step detection unit 180 stands by until the vertical velocity is set to be equal to or less than the threshold (step B15; No). When the vertical velocity is set to be equal to less than the threshold (step B15; Yes), the process returns to step B11.

Referring back to the traveling direction velocity calculation process of FIG. 8, when the one-step detection process is started, the posture calculation unit 130 determines whether a timing at which the sensor posture is calculated has arrived (step A7). For example, as the timing at which the velocity in the traveling direction is calculated, the counter "n" is set to an odd number, it is determined whether the counter "n" is set to an odd number.

When it is determined not to be the timing at which the sensor posture is calculated (step A7; No), the posture calculation unit 130 stands by at it is. On the other hand, when it is determined to be the timing at which the sensor posture is calculated (step A7; Yes), the posture calculation unit 130 calculates the sensor posture (step A9). Specifically, the sensor posture angles (pitch angle "θ" and yaw angle "ψ") are calculated in accordance with Expressions (2) and (3), and are stored as the posture data 650 in the storage unit 600.

Thereafter, the LV coordinate transformation matrix calculation unit 140 calculates the LV coordinate transformation matrix using the sensor posture angle which is stored in the posture data 650, and stores the resultant in the coordinate transformation matrix data 660 of the storage unit 600 (step A11).

Next, the traveling direction velocity calculation unit 170 determines whether it is the timing at which the traveling direction velocity is calculated (step A13). This is a timing at which the same condition as that of step A7 is satisfied. For example, when step A7 is a timing at which the counter "n" is set to an odd number, step A13 is also a timing at which the counter "n" is set to an odd number.

When it is determined not to be the timing at which the traveling direction velocity is calculated (step A13; No), the processing unit 100 causes the process to transition to step A23. On the other hand, when it is determined to be the timing at which the traveling direction velocity is calculated (step A13; Yes), the processing unit 100 extracts the detection result (local coordinate acceleration vector) of the acceleration sensor 10 for a target period from the local coordinate velocity vector data 640 of the storage unit 600 (step A15). The target period is, for example, a period from the timing at which the traveling direction velocity is calculated back to a timing at which the most recent vertical velocity exceeds the threshold. This is a period until one foot lands and then a step of the foot is taken, and the body reaches the highest point.

Next, the mobile body coordinate acceleration vector calculation unit 150 performs a mobile body coordinate acceleration vector calculation process (step A17). Specifically, coordinate transformation is performed on the detection result (local coordinate acceleration vector) of the acceleration sensor 10 extracted in step A15, using the LV coordinate transformation matrix which is stored in the coordinate transformation matrix data 660, to calculate the mobile body coordinate acceleration vector, and the resultant is stored in the mobile body coordinate acceleration vector data 670 of the storage unit 600.

Thereafter, the traveling direction acceleration amplitude calculation unit 160 calculates the traveling direction acceleration amplitude (step A19). Specifically, a maximum value and a minimum value of the latest traveling direction acceleration is extracted from a variation over time of the traveling direction acceleration included in the mobile body coordinate velocity vector calculated in step A17, and the difference therebetween is calculated as the traveling direction acceleration amplitude.

Next, the traveling direction velocity calculation unit 170 calculates the traveling direction velocity (step A21). Specifically, the traveling direction velocity is calculated by substituting the traveling direction acceleration amplitude calculated in step A19 into the correlation expression which is stored in the correlation expression data 620 of the storage unit 600, and the resultant is stored in the traveling direction velocity data 680 of the storage unit 600.

Thereafter, the processing unit 100 determines whether the process is terminated (step A23). When it is determined that the process is continuing (step A23; No), the process returns to step A13. In addition, when it is determined that the process has terminated (step A23; Yes), the traveling direction velocity calculation process is terminated.

1-4. Operational Effects

In the traveling direction velocity calculation device 1 which is worn on a user's body, the posture of the acceleration sensor 10 with respect to a user is calculated using a detection result represented in the local coordinate system associated with the acceleration sensor 10 that detects acceleration when a change in the detection result satisfies a predetermined specific condition. The detection result of the acceleration sensor 10 at a time different from that when the posture is calculated and at a time when the specific condition is satisfied is transformed, using the calculated posture, to the mobile body coordinate system associated with the user. The velocity in the traveling direction of the user is calculated using the transformed detection result of the acceleration sensor 10.

Specifically, when the vertical velocity is set to a value of a central portion in a varying range on the basis of a change in the vertical velocity obtained from the detection result of the acceleration sensor 10, and the direction of change of the velocity is an increasing direction (highest point arrival timing), it is determined that the specific condition is satisfied. The sensor posture angle of the acceleration sensor 10 is then calculated using the detection result of the acceleration sensor 10 at the highest point arrival timing. The LV coordinate transformation matrix is calculated using the calculated sensor posture angle, coordinate transformation is performed on the detection result of the acceleration sensor 10 to the mobile body coordinate using the calculated matrix, and the traveling direction acceleration amplitude of the user is calculated. The traveling direction velocity of the user is calculated on the basis of a given correlation between the calculated traveling direction acceleration amplitude and the traveling direction velocity.

The traveling direction velocity is calculated in accordance with a timing at which it is considered that the postures of the acceleration sensor 10 with respect to the user becomes the same as each other, and thus the traveling direction velocity of the user can be appropriately calculated regardless of whether the user's motion is walking or running. In addition, based on a given correlation between the traveling direction acceleration amplitude and the traveling direction velocity, the traveling direction velocity of a user can be calculated more accurately than in the related art.

The determination of a timing at which the specific condition is satisfied is performed by detecting that the vertical velocity calculated on the basis of the detection result of the acceleration sensor 10 is set to a value of a central portion in a varying range, and that the direction of change of the velocity is an increasing direction. This is a timing (highest point arrival timing) at which the body reaches a highest arrival point. Since the sensor posture is calculated using this highest point arrival timing as a timing at which the specific condition is satisfied, and then the traveling direction velocity is calculated intermittently at a timing at which it is considered that the sensor posture becomes the same, it is possible to calculate the traveling direction velocity of the user with a high level of accuracy.

2. Second Embodiment 2-1. Functional Configuration

Figure 10:
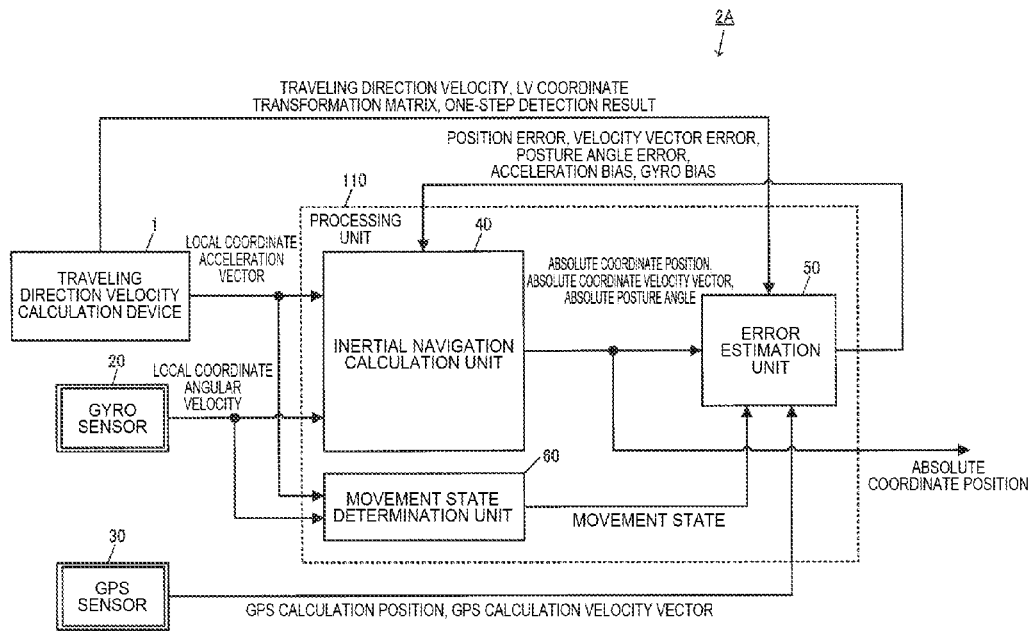
FIG. 10 is a diagram illustrating an outline of a functional configuration of a position calculation device.

FIG. 10 is a diagram illustrating an outline of a functional configuration of a position calculation device 2A according to a second embodiment. The position calculation device 2A is a device which is added to the function of the traveling direction velocity calculation device 1 of the first embodiment. In order to make the description thereof easier to understand, FIG. 10 shows a configuration in which the position calculation device 2A includes the traveling direction velocity calculation device 1, but in reality, the position calculation device can be configured such that a function of a processing unit 110 of FIG. 10 is added to the processing unit 100 of the traveling direction velocity calculation device 1, and that a gyro sensor 20 and a GPS (Global Positioning System) sensor 30 are further added to the traveling direction velocity calculation device 1.

Meanwhile, similarly to the traveling direction velocity calculation device 1, the position calculation device 2A is, for example, a type of movement state information calculation device, used in a state where the device worn on a user's waist (right waist or left waist), which performs calculation in a state where a position is included in movement state information in addition to the traveling direction velocity of a user.

The gyro sensor 20 is a sensor that detects an angular velocity of a user, and detects an angular velocity (hereinafter, referred to as a "local coordinate angular velocity") using the same local coordinate system as that of the acceleration sensor 10 included in the traveling direction velocity calculation device 1. The detected local coordinate angular velocity is output to an inertial navigation calculation unit 40.

The GPS sensor 30 is a sensor that receives a GPS satellite signal transmitted from a GPS satellite which is a type of positioning satellite, and calculates the position and velocity vector of a user using the GPS satellite signal. The GPS sensor 30 calculates the position and velocity vector (velocity and orientation) of a user in a given absolute coordinate system, and outputs the resultant to an error estimation unit 50 as a GPS calculation position and a GPS calculation velocity vector. Meanwhile, a method of calculating a position and a velocity vector using a GPS is hitherto known, and thus the description thereof will not be given.

The processing unit 110 is configured to include the inertial navigation calculation unit 40, the error estimation unit 50, and a movement state determination unit 60. As described above, the processing unit 100 of the traveling direction velocity calculation device 1 may have these functional units added thereto, and may be configured as a separate processor or the like.

The inertial navigation calculation unit 40 performs a known inertial navigation calculation process using a local coordinate acceleration vector which is output from the traveling direction velocity calculation device 1 and a local coordinate angular velocity which is output from the gyro sensor 20, and calculates a position (absolute coordinate position), a velocity vector (absolute coordinate velocity vector) and a posture angle (absolute posture angle) of a user in the absolute coordinate system.

The inertial navigation calculation unit 40 corrects the local coordinate acceleration vector which is output from the acceleration sensor 10 of the traveling direction velocity calculation device 1 and the local coordinate angular velocity which is output from the gyro sensor 20, using an acceleration bias and a gyro bias which are output from the error estimation unit 50. The absolute coordinate position, the absolute coordinate velocity vector and the absolute posture angle are calculated using the local coordinate acceleration vector and the local coordinate angular velocity after correction, and the absolute coordinate position, the absolute coordinate velocity vector and the absolute posture angle are corrected using a position error, a velocity vector error and a posture angle error which are output from the error estimation unit 50.

The error estimation unit 50 controls and inputs inertial navigation calculation results (absolute coordinate position, absolute coordinate velocity vector and absolute posture angle) which are output from the inertial navigation calculation unit 40, performs error estimation calculation (hereinafter, referred to as a "KF error estimation calculation") using, for example, a Kalman filter (hereinafter, denoted by "KF"), and estimates an error included in the inertial navigation calculation results (hereinafter, referred to as an "inertial navigation calculation error"). The estimated inertial navigation calculation error is then output to the inertial navigation calculation unit 40 in a feedback manner. In the present embodiment, the inertial navigation calculation error includes a position error, a velocity vector error, a posture angle error, an acceleration bias and a gyro bias.

The inertial navigation calculation unit 40 and the error estimation unit 50 are equivalent to a movement state information calculation unit that calculates movement state information of a user using the posture of a sensor with respect to a user and the detection result of the sensor.

The movement state determination unit 60 determines a movement state of a user on the basis of the local coordinate acceleration vector which is output from the acceleration sensor 10 and the local coordinate angular velocity which is output from the gyro sensor 20. In the present embodiment, as the movement state of a user, it is determined whether the user is in a state of stop (hereinafter, referred to as a "stop state"), or the user is in a state of movement (hereinafter, referred to as a "movement state").

The inertial navigation calculation unit 40, the error estimation unit 50, and the movement state determination unit 60 can be configured as the processing unit 110 having a processor such as a CPU or a DSP.

2-2. Flow of Processes

Figure 11:
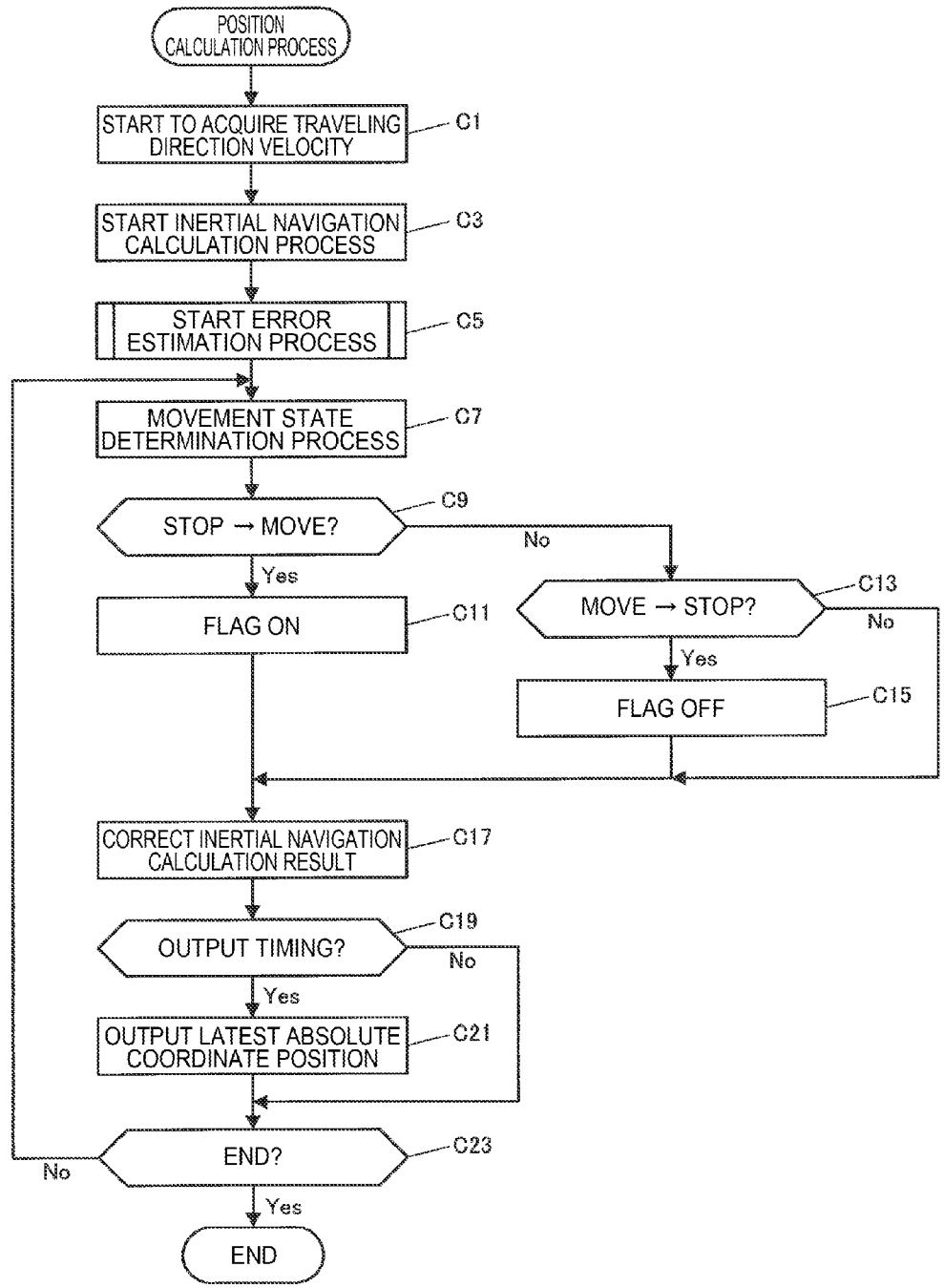
FIG. 11 is a flow diagram illustrating a flow of a position calculation process.

FIG. 11 is a flow diagram illustrating a flow of a position calculation process which is executed by the processing unit 110 of the position calculation device 2A.

Initially, the inertial navigation calculation unit 40 starts to acquire the traveling direction velocity from the traveling direction velocity calculation device 1 (step C1). Thereafter, the inertial navigation calculation unit 40 starts an inertial navigation calculation process (step C3). The error estimation unit 50 starts an error estimation process described later (step C5).

Next, the movement state determination unit 60 performs a movement state determination process (step C7). Thereafter, the processing unit 110 determines whether the movement state changes from the stop state to the movement state (step C9). When the determination result is positive (step C9; Yes), a flag is set to ON (step C11).

On the other hand, when the determination result of step C9 is negative (step C9; No), the processing unit 110 determines whether the movement state changes from the movement state to the stop state (step C13). When the determination result is positive (step C13; Yes), the processing unit 110 set a flag to OFF (step C15).

After step C11 or C15, or when the determination result of step C13 is negative (step C13; No), the inertial navigation calculation unit 40 corrects the inertial navigation calculation results using the latest inertial navigation calculation error estimated by the error estimation unit 50 (step C17).

Thereafter, the inertial navigation calculation unit 40 determines whether being an output timing of a position (step C19). When it is determined to be an output timing (step C19; Yes), the latest absolute coordinate position is output (step C21). When it is determined not to be an output timing (step C19; No), the process transitions to step C23.

Next, the processing unit 110 determines whether the process has terminated (step C23). When it is determined that the process is continuing (step C23; No), the process returns to step C7. On the other hand, when it is determined that the process has terminated (step C23; Yes), the processing unit 110 terminates the position calculation process.

Figure 12:
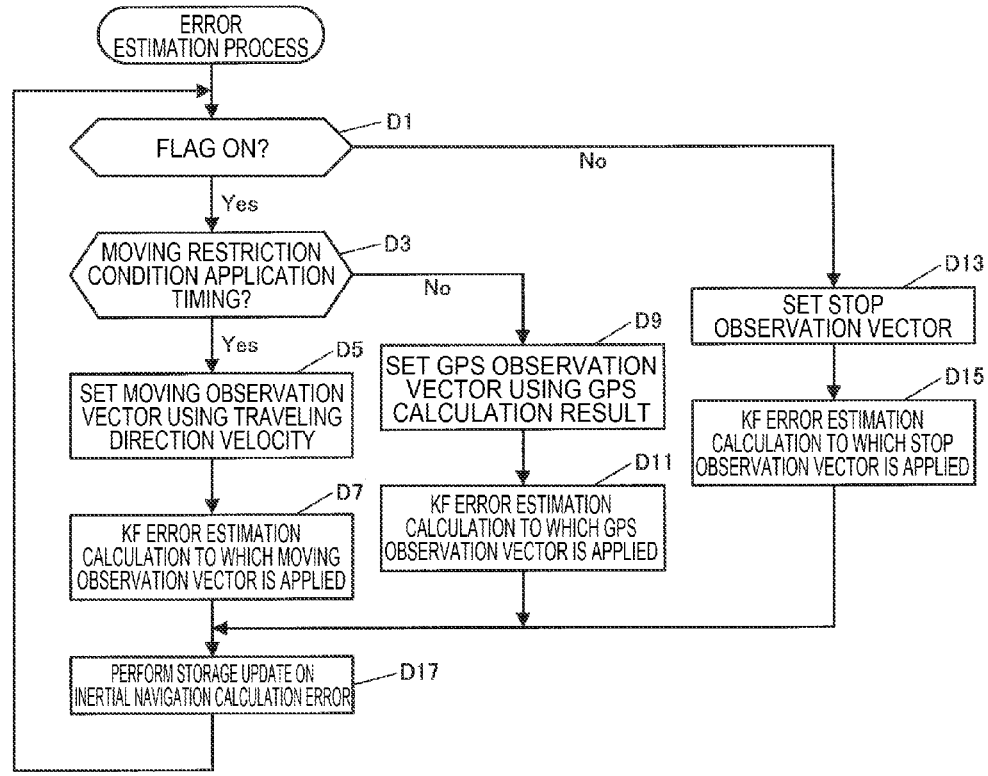
FIG. 12 is a flow diagram illustrating of a flow of an error estimation process.

FIG. 12 is a flow diagram illustrating a flow of an error estimation process.

In the error estimation process, the error estimation unit 50 performs the KF error estimation calculation by setting a state vector X as shown in the following Expression (4).

Expression 4

$$X = \begin{bmatrix} \delta P \\ \delta V \\ \delta A \\ b_a \\ b_w \end{bmatrix} \quad (4)$$

Herein "$\delta P$", "$\delta V$" and "$\delta A$" are the position error, the velocity vector error and posture angle error which are included in the calculation result of the inertial navigation calculation unit 40, respectively. In addition, "$b_a$" and "$b_w$" are the acceleration bias and the gyro bias, respectively.

Initially, the error estimation unit 50 determines whether a flag is set to ON (step D1). When it is determined that the flag is set to ON (step D1; Yes), it is determined whether being an application timing of a moving restriction condition (step D3). The application timing of a moving restriction condition is the same timing as the traveling direction velocity calculation timing (step A13 of FIG. 8) based on the traveling direction velocity calculation device 1. That is, this is a timing at which every other highest point arrival timing arrives.

When it is determined to be the application timing of a moving restriction condition (step D3; Yes), the error estimation unit 50 sets a moving observation vector using the traveling direction velocity which is output from the traveling direction velocity calculation device 1 (step D5).

Specifically, the posture angle is calculated using the angular velocity which is output from the gyro sensor 20, and a coordinate transformation matrix from the absolute coordinate system to the local coordinate system (hereinafter, referred to as an "AL coordinate transformation matrix") is calculated using the calculated posture angle. The absolute coordinate velocity vector calculated by the inertial navigation calculation unit 40 is then transformed into the mobile body coordinate velocity vector using the calculated AL coordinate transformation matrix and the LV coordinate transformation matrix which is output from the traveling direction velocity calculation device 1. A moving observation vector $Z_{move}$ as shown in, for example, the following Expression (5) is set using a traveling direction velocity V which is output from the traveling direction velocity calculation device 1 and the calculated mobile body coordinate velocity vector $v^V = (v^V_R, v^V_P, v^V_Q)^T$.

Expression 5

$$Z_{move} = \begin{bmatrix} |V| \\ 0 \\ 0 \end{bmatrix} - \begin{bmatrix} v^V_R \\ v^V_P \\ v^V_Q \end{bmatrix} \quad (5)$$

The moving observation vector $Z_{move}$ is an observation vector which is set on the basis of the assumption that the velocity component in the longitudinal and transverse directions (vertical direction and horizontal direction) of a user is zero. That is, in a timing at which the highest point arrival timing arrives, it is assumed that velocity components of the mobile body coordinate system (V frame) in the Q-axis direction and the P-axis direction are set to be zero, and that a velocity component equivalent to the traveling direction velocity V is generated in the R-axis direction which is a traveling direction, and the moving observation vector $Z_{move}$ as mentioned above is set.

In this case, the error estimation unit 50 performs the KF error estimation calculation to which the moving observation vector $Z_{move}$ which is set in step D5 is applied (step D7). That is, the moving observation vector $Z_{move}$ which is set in step D5 is used as observation information, and the inertial navigation calculation error is estimated by performing predetermined prediction calculation and correction calculation.

The moving observation vector $Z_{move}$ is set using the traveling direction velocity calculated on the basis of the amplitude of traveling direction acceleration. In addition, the velocity vector error of a user is included in the inertial navigation calculation error estimated by the error estimation unit 50, and the absolute coordinate velocity vector calculated by the inertial navigation calculation unit 40 is calculated using the detection result of the acceleration sensor 10. Therefore, the estimation of the inertial navigation calculation error using the moving observation vector $Z_{move}$, and the correction of the inertial navigation calculation results are equivalent to the correction of a velocity indicated by the detection result of the sensor using the traveling direction velocity calculated on the basis of the amplitude of traveling direction acceleration, and the calculation of the movement state information of a user.

In step D3, when it is determined not to be the moving restriction condition application timing (step D3; No), the error estimation unit 50 sets a GPS observation vector using a GPS calculation result which is output from the GPS sensor 30 (step D9). That is, a GPS observation vector using the GPS calculation position and the GPS calculation velocity vector as a component is set.

Next, the error estimation unit 50 performs the KF error estimation calculation to which the set GPS observation vector is applied (step D11). That is, the GPS observation vector which is set in step D9 is used as observation information, and the inertial navigation calculation error is estimated by performing the predetermined prediction calculation and the correction calculation.

In step D1, when it is determined that a flag is set to OFF (step D1; No), the error estimation unit 50 sets a stop observation vector (step D13). Specifically, the stop observation vector $Z_{stop}$ as shown in, for example, the following Expression (6) is set using the absolute coordinate velocity vector $V^A = (V^A_X, V^A_Y, V^A_Z)^T$ calculated by the inertial navigation calculation unit 40.

Expression 6

$$Z_{stop} = \begin{bmatrix} 0 \\ 0 \\ 0 \end{bmatrix} - \begin{bmatrix} v_X^A \\ v_Y^A \\ v_Z^A \end{bmatrix} \quad (6)$$

The stop observation vector $Z_{stop}$ is an observation vector which is set on the basis of the assumption that the velocity component of a user is zero. That is, in the stop state, it is assumed that the velocity component in the direction of each axis in the absolute coordinate system (A frame) is set to be zero, and the stop observation vector $Z_{stop}$ as mentioned above is set.

In this case, the error estimation unit 50 performs the KF error estimation calculation to which the stop observation vector $Z_{stop}$ which is set in step D13 is applied (step D15). That is, the stop observation vector $Z_{stop}$ which is set in step D15 is used as observation information, and the inertial navigation calculation error is estimated by performing the predetermined prediction calculation and the correction calculation.

After step D7, D11 or D15, the error estimation unit 50 performs storage update on the inertial navigation calculation error estimated in the KF error estimation calculation (step D17). The error estimation unit 50 then returns to step D1.

2-3. Experimental Result

Figure 13:
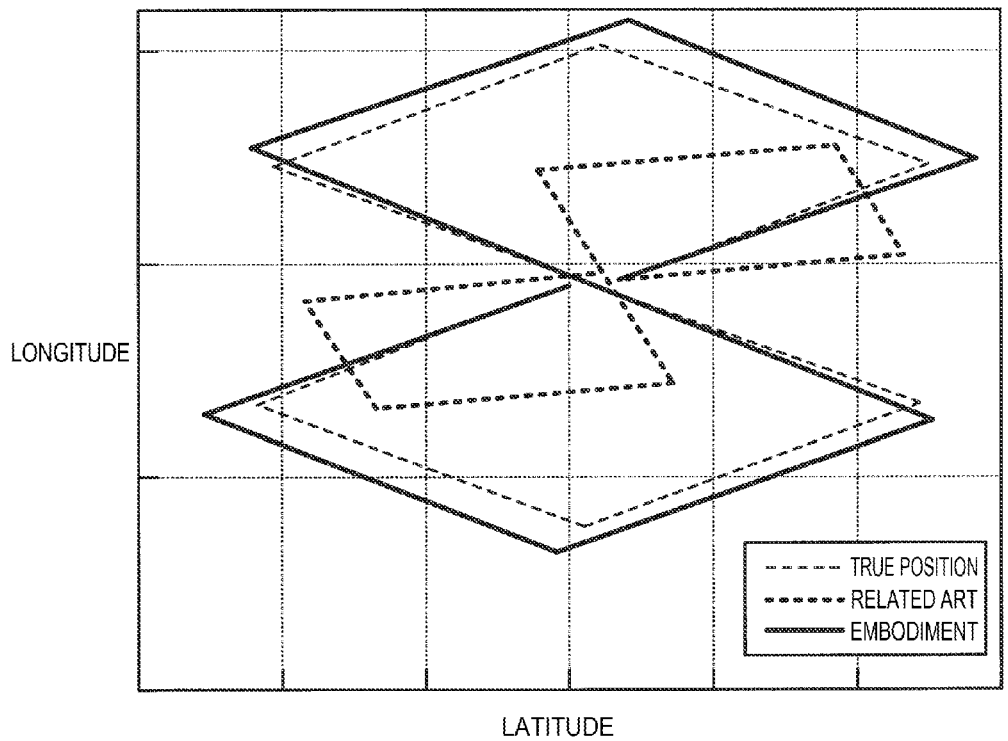
FIG. 13 is a diagram illustrating an example of experimental results obtained by performing position calculation.

FIG. 13 is a diagram illustrating experimental results obtained by performing the position calculation in the position calculation device 2A. An experiment of calculating a position by causing a test subject wearing the position calculation device 2A to run along a predetermined path has been performed. In FIG. 13, the horizontal axis is longitude, and the vertical axis is latitude. In addition, the trajectory of a true position is shown by a thin broken line, the trajectory of a calculated position when the position calculation is performed using a method of the related art is shown by a thick broken line, and the trajectory of a calculated position when the position calculation is performed using a method of the present embodiment is shown by a solid line. Meanwhile, as the method of the related art, a method is used in which the posture of a sensor with respect to a user which is calculated at a certain timing independent of a timing at which the specific condition is satisfied is used in the traveling direction velocity calculation at any subsequent timing.

From such results, it can be understood that the trajectory of a calculated position when the position calculation is performed using the method of the related art is changed to a trajectory which is reduced on the whole with respect to the trajectory of a true position, and that the position shifts greatly. On the other hand, it can be confirmed that the trajectory of a calculated position when the position calculation is performed using the method of the present embodiment is changed to a trajectory close to the true trajectory, and that the accuracy of the position calculation improves more greatly than in a case where the method of the related art is used.

2-4. Operational Effect

In the position calculation device 2A, the inertial navigation calculation unit 40 performs the inertial navigation calculation process using the local coordinate acceleration vector which is output from the traveling direction velocity calculation device 1 and the local coordinate angular velocity which is output from the gyro sensor 20, and calculates the position, the velocity vector and the posture angle of a user in the absolute coordinate system. The error estimation unit 50 estimates an error included in the inertial navigation calculation results calculated by the inertial navigation calculation unit 40. The inertial navigation calculation unit 40 then corrects the inertial navigation calculation results using the inertial navigation calculation error estimated by the error estimation unit 50.

The error estimation unit 50 sets the moving observation vector using the traveling direction velocity which is output from the traveling direction velocity calculation device 1 and the mobile body coordinate velocity vector. The KF error estimation calculation to which the moving observation vector is applied is then performed so as to be synchronized with the traveling direction velocity calculation timing, and thus it is possible to appropriately estimate the inertial navigation calculation error without being influenced by a change in the sensor posture associated with the walking motion or running motion of a user. As a result, the inertial navigation calculation results are corrected using the inertial navigation calculation error, it is possible to appropriately calculate the movement state information such as the position and velocity of a user.

In addition, in the KF error estimation calculation, the error estimation unit 50 estimates a bias (acceleration bias) included in the detection result of the acceleration sensor 10 or a bias (gyro bias) included in the detection result of the gyro sensor 20, in addition to the error included in the position, the velocity vector, and the posture angle. The bias of a sensor becomes a factor for a large error when the inertial navigation calculation is performed. However, the inertial navigation calculation unit 40 corrects the detection result of the acceleration sensor 10 or the detection result of the gyro sensor 20, using the acceleration bias or the gyro bias estimated by the error estimation unit 50, and the inertial navigation calculation process is performed using the corrected result, thereby allowing the movement state information of a user to be calculated with a high level of accuracy.

3. Third Embodiment

Figure 14:
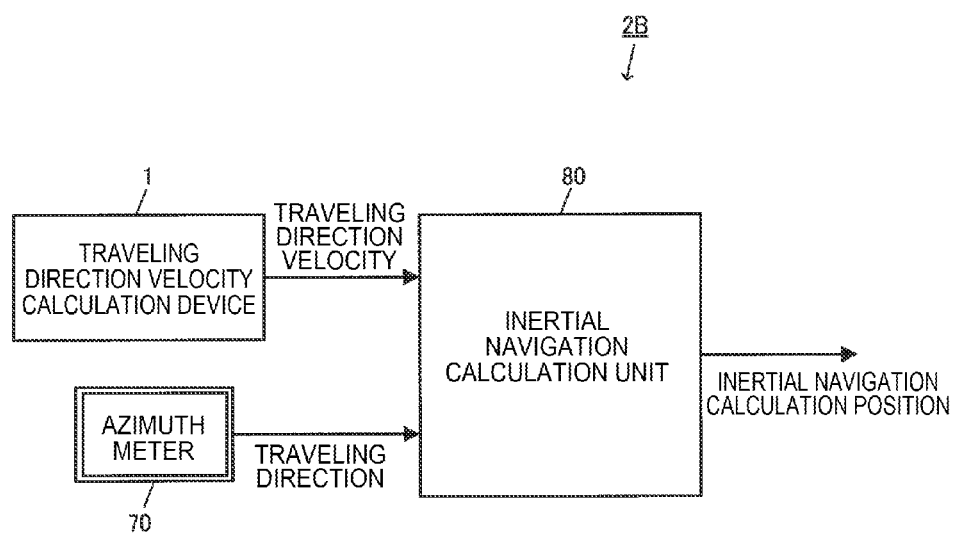
FIG. 14 is a diagram illustrating an outline of a functional configuration of the position calculation device.

FIG. 14 is a diagram illustrating an outline of a position calculation device 2B in a third embodiment.

The position calculation device 2B is a device which is added to the function of the traveling direction velocity calculation device 1 of the first embodiment. In order to make the description thereof easier to understand, FIG. 14 shows a configuration in which the position calculation device 2B includes the traveling direction velocity calculation device 1, but in reality, the position calculation device can be configured such that a function of an inertial navigation calculation unit 80 of FIG. 14 is added to the processing unit 100 of the traveling direction velocity calculation device 1, and that an azimuth meter 70 is further added to the traveling direction velocity calculation device 1.

Meanwhile, similarly to the traveling direction velocity calculation device 1, the position calculation device 2B is, for example, a type of movement state information calculation device, used in a state where the device worn on a user's waist (right waist or left waist), which performs calculation in a state where a position is included in movement state information in addition to the traveling direction velocity of a user.

The traveling direction velocity calculation device 1 is the traveling direction velocity calculation device 1 of the first embodiment, and calculates the traveling direction velocity of a user, to output the result to the inertial navigation calculation unit 80.

The azimuth meter 70 is an azimuth measuring device that detects the traveling direction of a user, and is configured to include an orientation sensor such as a magnetic sensor. The azimuth meter 70 outputs the measured traveling direction (orientation) of a user to the inertial navigation calculation unit 80.

The inertial navigation calculation unit 80 performs a known inertial navigation calculation process using a traveling direction velocity which is output from the traveling direction velocity calculation device 1 and a traveling direction which is output from the azimuth meter 70, and calculates the position of a user. In the present embodiment, the inertial navigation calculation unit 80 is equivalent to a movement state information calculation unit that calculates movement state information of a user using the posture of a sensor with respect to a user and the detection result of the sensor.

4. Modification Example

Embodiments to which the invention can be applied are not limited to the above first to third embodiments, and changes and modifications can be appropriately made, of course, without departing from the scope of the invention. Hereinafter, a modification example will be described. Meanwhile, the same components as those in the above embodiments are denoted by the same reference numerals and signs, the description thereof will not be repeated.

4-1. Type of Sensor

In the above-mentioned embodiments, the acceleration sensor 10 has been described as a sensor worn on a user's body, but a velocity sensor that detects the velocity of a user rather than the acceleration sensor 10 may be worn on a user's body. In this case, the traveling direction velocity calculation device 1 or the position calculation devices 2A and 2B including the velocity sensor may be worn on a predetermined region of a user's body.

4-2. Wearing Region of Sensor

In the above-mentioned embodiments, the waist has been described as the wearing region of the sensor (traveling direction velocity calculation device 1 or position calculation devices 2A and 2B) on a user's body, but the sensor may be worn on regions other than the waist. A suitable wearing region is a user's trunk (regions other than the arms and legs). However, the sensor may be worn on, for example, a user's head or foot other than the arm without being limited to the trunk.

4-3. Posture Calculation Timing and Traveling Direction Velocity Calculation Timing In the above-mentioned embodiments, every other highest point arrival timing has been described as the traveling direction velocity calculation timing, but the traveling direction velocity calculation may be performed at each highest point arrival timing.

Figure 15:
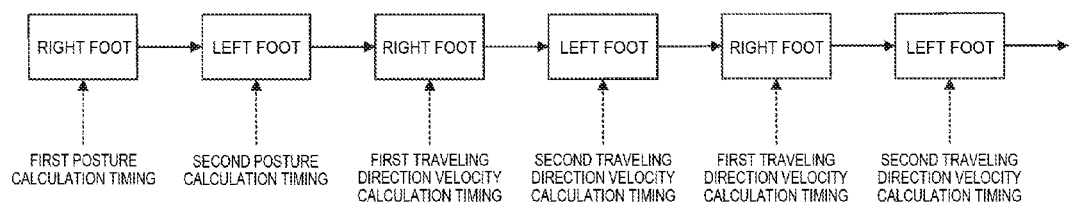
FIG. 15 is a diagram illustrating a modification example of posture calculation timings and traveling direction velocity calculation timings.

FIG. 15 is a diagram illustrating a traveling direction velocity calculation timing in this case.

A first sensor posture is calculated by setting the highest point arrival timing relating to the right foot (highest point arrival timing from landing of the right foot to landing of the left foot) to a first posture calculation timing. A second sensor posture is calculated by setting the highest point arrival timing relating to the next left foot (highest point arrival timing from landing of the left foot to landing of the right foot) to a second posture calculation timing. Thereafter, a first traveling direction velocity is calculated using the first sensor posture whenever the highest point arrival timing relating to the right foot arrives, and a second traveling direction velocity is calculated using the second sensor posture whenever the highest point arrival timing relating to the left foot arrives. Meanwhile, a method of calculating a sensor posture and a method of calculating a traveling direction velocity are the same as those in the above-mentioned embodiments.

A case where the modification example is applied to the position calculation device 2A described in the second embodiment is as follows. The error estimation unit 50 estimates the inertial navigation calculation error by performing the KF error estimation calculation in which a first moving observation vector which is set using the first traveling direction velocity is used as observation information so as to be synchronized with the highest point arrival timing relating to the right foot. In addition, the inertial navigation calculation error is estimated by performing the KF error estimation calculation in which a second moving observation vector which is set using the second traveling direction velocity is used as observation information so as to be synchronized with the highest point arrival timing relating to the left foot.

In addition, as in the above embodiments or the above modification example, the highest point arrival timing is not set to the posture calculation timing or the traveling direction velocity calculation timing, and the landing timing of one foot or each foot may be set to the posture calculation timing or the traveling direction velocity calculation timing. The determination of the landing timing can be realized by determining a timing at which the vertical velocity is set to a value of a central portion in a varying range, and the direction of change of the velocity is set to a decreasing direction.

In addition, the sensor posture may be sequentially calculated on the basis of the detection result of the acceleration sensor 10 at each sample timing, and the traveling direction velocity may be calculated by setting a corresponding sample timing of the acceleration sensor 10 to the traveling direction velocity calculation timing whenever one step is detected.

In addition, the calculated sensor posture may be used in the calculation of the traveling direction velocity at a timing prior to a timing at which the sensor posture is calculated. For example, the one-step detection process may be performed on the detection result of the acceleration sensor 10 before a point in time when the posture calculation process (step A9) is performed, which is stored in the sensor detection data 630 of the storage unit 600, and the traveling direction velocity may be calculated by determining the traveling direction velocity calculation timing.

In addition, as in the above-mentioned embodiment, the sensor posture does not have to be calculated on the basis of the detection result of the acceleration sensor 10 at any one timing. For example, the sensor posture may be calculated using an average value of the detection result of the acceleration sensor 10 corresponding to one step. In addition, the sensor posture may be sequentially calculated on the basis of the detection result of the acceleration sensor 10 at each sample timing, and a value obtained by averaging the sensor postures corresponding to one step may be set to the sensor posture in the one step. In these cases, it is preferable that each sensor posture be calculated in case where the right foot is planted and in case where the left foot is planted.

4-4. Method of Calculating Sensor Posture

In the second embodiment, the posture of a sensor with respect to a user may be calculated using the absolute coordinate velocity vector included in the inertial navigation calculation results calculated by the inertial navigation calculation unit 40. Specifically, the absolute coordinate velocity vector calculated by the inertial navigation calculation unit 40 is coordinate-transformed to the local coordinate velocity vector using the absolute posture angle. Using the local coordinate velocity vector, the sensor posture is calculated in accordance with Expressions (2) and (3).

4-5. Error Estimation

In the above-mentioned embodiments, a description has been given in which, after the sensor posture is once calculated at the posture calculation timing, the traveling direction velocity is calculated using the above sensor posture at the traveling direction velocity calculation timing. However, it is considered that even at a timing at which the postures are considered to be the same as each other while a user is walking or running, the posture of a sensor with respect to the user changes slightly. Consequently, the following may be performed.

The error estimation unit 50 estimates an error angle of an installation state by adding a component of an error angle due to a change in the sensor posture, that is, a change in the installation state to the state vector X used in the KF error estimation calculation, and performing the same KF error estimation calculation as that in the above-mentioned embodiments. The sensor posture may be update using the error angle of the installation state, and the traveling direction velocity may be calculated using the updated sensor posture at the traveling direction velocity calculation timing.

4-6. Correction of Detection Result of Sensor

A value of a component other than a traveling direction component of a user included in the detection result of the sensor may be corrected. Specifically, in the traveling direction velocity calculation device 1 of the above-mentioned embodiment, after the sensor posture is calculated, the LV coordinate transformation matrix is calculated using the sensor posture. The local coordinate acceleration vector of the acceleration sensor 10 is then coordinate-transformed to the mobile body coordinate acceleration vector using this LV coordinate transformation matrix. The mobile body coordinate acceleration vectors are integrated and added to thereby calculate the mobile body coordinate velocity vectors, and a value other than a traveling direction component of the mobile body coordinate velocity vector is corrected to zero. Thereby, the traveling direction velocity of a user can be calculated in a method different from the method of calculating a traveling direction velocity described in the first embodiment.

The mobile body coordinate velocity vector is calculated on the basis of the mobile body coordinate acceleration vector, and the mobile body coordinate acceleration vector is calculated on the basis of the local coordinate acceleration vector. Therefore, the correction of a value other than a traveling direction component of the mobile body coordinate velocity vector to zero is equivalent to the correction of a value of a component other than a traveling direction component of a user included in the detection result of the sensor.

4-7. Correlation Characteristics

In the above-mentioned embodiments, a fixed correlation expression which is set in advance has been described as the correlation expression indicating a correlation between the traveling direction acceleration amplitude and the traveling direction velocity. However, a step length or a walking velocity varies for each user. For this reason, a correlation expression may be created for each user.

In this case, the traveling direction velocity of a user over a fixed period is calculated in the method described in, for example, "4-6. Correction of Detection Result of Sensor", and sample data associated with the traveling direction acceleration amplitude of a user is stored. A correlation expression may be calculated in a method such as a least-squares method using the sample data, and may be stored in the correlation expression data 620 of the storage unit 600.

4-8. Component of Posture Determination

In the above-mentioned embodiments, a description has been given of the determination of both the pitch component and the yaw component of the posture of the sensor with respect to the user, but only any one of the pitch component and the yaw component may be, of course, determined.

4-9. Method of One-step Detection Process

In the above-mentioned embodiment, a description has been given of the performing of one-step detection by determining a timing at which the vertical velocity is set to a value of a central portion in a varying range, and the direction of change of the velocity is set to an increasing direction or a decreasing direction. However, a timing at which the sensor posture is calculated may be determined by performing other known one-step detection processes. For example, a timing at which a vertical velocity or vertical acceleration is set to a minimum value or a maximum value may be determined. In addition, data may be used in which a filtering process of removing high-frequency noise from the detection result of the sensor is performed.

The entire disclosure of Japanese Patent Application No. 2013-061456, filed on Mar. 25, 2013, is expressly incorporated by reference herein.

The invention claimed is:

1. A movement state information calculation method comprising:
   using a processing unit:
   calculating a posture of a sensor with respect to a user, using a detection result represented in a coordinate system associated with the sensor, detecting any of a velocity and acceleration, which is worn on a user's body, when a change in the detection result satisfies a predetermined specific condition;
   transforming the detection result at a time different from that when the posture is calculated and at a time when the specific condition is satisfied, using the posture, to a mobile body coordinate system associated with the user; and
   calculating movement state information which is any of a position and a velocity of the user, using the transformed detection result.

2. The movement state information calculation method according to claim 1, further comprising correcting a value of a component other than a traveling direction component of the user included in the transformed detection result.

3. The movement state information calculation method according to claim 2, wherein calculating the movement state information includes:
   calculating an amplitude of acceleration in a traveling direction of the user, using the transformed detection result; and
   calculating a velocity in a traveling direction of the user on the basis of the amplitude.

4. The movement state information calculation method according to claim 1, wherein calculating the movement state information includes:

calculating an amplitude of acceleration in a traveling direction of the user, using the transformed detection result; and calculating a velocity in a traveling direction of the user on the basis of the amplitude.

5. The movement state information calculation method according to claim 1, wherein calculating the posture includes determining a timing at which the specific condition is satisfied on the basis of a change in a vertical velocity which is obtained from the detection result of the coordinate system associated with the sensor.

6. The movement state information calculation method according to claim 5, wherein determining the timing includes determining that the specific condition is satisfied when the vertical velocity is set to a value of a central portion in a varying range, and a direction of change of the velocity is an increasing direction or a decreasing direction.

7. The movement state information calculation method according to claim 1, wherein the sensor is worn on a predetermined region other than an arm of the user.

8. A movement state information calculation device comprising:

a sensor, detecting any of a velocity and acceleration, which is worn on a user's body; and a processing unit, wherein the processing unit includes:

a posture calculation unit that calculates a posture of the sensor with respect to the user, using a detection result of the sensor represented in a coordinate system associated with the sensor when a change in the detection result satisfies a predetermined specific condition;

a coordinate transformation matrix calculation unit that calculates a coordinate transformation matrix which is used for transforming the detection result at a time different from that when the posture is calculated and at a time when the specific condition is satisfied, using the posture, to a mobile body coordinate system associated with the user; and a movement state information calculation unit that calculates movement state information of the user, using the coordinate transformation matrix, and the detection result at a time different from that when the posture is calculated and at a time when the specific condition is satisfied.

* * * * *